United States Patent [19]

Kissel

[11] Patent Number: 5,861,170
[45] Date of Patent: Jan. 19, 1999

[54] ACETYLSALICYCLIC ACID-CONTAINING TRANSDERMAL APPLICATION SYSTEM FOR ANTITHROMBOTIC THERAPY

[75] Inventor: Thomas Kissel, Staufen, Germany

[73] Assignee: LTS Lohmann Therapie-Systeme GmbH & Co. KG, Neuwied, Germany

[21] Appl. No.: 216,089

[22] Filed: Mar. 22, 1994

Related U.S. Application Data

[63] Continuation of Ser. No. 957,280, Oct. 6, 1992, abandoned.

[30] Foreign Application Priority Data

Dec. 20, 1991 [DE] Germany .......................... 41 42 483.2

[51] Int. Cl.$^6$ ..................................................... A61F 13/02
[52] U.S. Cl. ........................................... 424/448; 424/449
[58] Field of Search ..................................... 424/448, 449

[56] References Cited

U.S. PATENT DOCUMENTS

| | | | |
|---|---|---|---|
| 3,598,122 | 8/1971 | Zaffaroni | 424/449 |
| 3,742,951 | 7/1973 | Zaffaroni | 128/268 |
| 3,797,494 | 3/1974 | Zaffaroni | 128/268 |
| 3,996,934 | 12/1976 | Zaffaroni | 128/268 |
| 4,012,508 | 3/1977 | Burton | 514/858 |
| 4,219,548 | 8/1980 | Reller | 514/786 |
| 4,460,368 | 7/1984 | Allison | 604/896 |
| 4,640,689 | 2/1987 | Sibalis | 424/449 |
| 4,665,063 | 5/1987 | Bar-Shalom | 514/164 |
| 4,810,699 | 3/1989 | Sabatucci et al. | 514/161 |
| 4,975,269 | 12/1990 | Chavkin et al. | 424/45 |

FOREIGN PATENT DOCUMENTS

| | | |
|---|---|---|
| 0162239 | 11/1985 | European Pat. Off. . |
| 61-167615 | 7/1986 | Japan . |
| 1-203336 | 8/1989 | Japan . |
| 1-242521 | 9/1989 | Japan . |

OTHER PUBLICATIONS

The Pharmacological Basis of Therapeutics, Gilman, Goodman and Gilman, Ed's pp. 1360–1361, 1980.
Fuster et al, *New England Journ. of Medicine* 321, 183–185 (1989); "Aspirin in the Prevention of Coronary Disease".
Buchanan et al, "Aspirin inhibits platelet function . . . " *Thrombosis Research* 25, 363–373 (1982).
Levy, "Clinical Pharmacokinetics of Aspirin", *Pediatrics* 62, 867=872 (1978).
Rowland et al, "Kinetics of Acetylsalicylic Acid Disposition in Man", *Nature* 215, 413–414 (1967).

*Primary Examiner*—D. Gabrielle Brouillette
*Attorney, Agent, or Firm*—Collard & Roe, P.C.

[57] ABSTRACT

A transdermal therapeutic system for antithrombotic therapy is disclosed. The system comprises a hydrophobic polymer matrix, acetic anhydride, and acetylsalicylic acid as the only active ingredient.

15 Claims, No Drawings

ACETYLSALICYCLIC ACID-CONTAINING TRANSDERMAL APPLICATION SYSTEM FOR ANTITHROMBOTIC THERAPY

This is a continuation of application Ser. No. 07/957,280 filed on Oct. 6, 1992 now abandoned.

DESCRIPTION

The platelet aggregation-preventing effect of acetylsalicylic acid (ASA) and its effect in the prevention of cardiac thrombosis was described in the late 60s. Subsequently, a large number of clinical studies were conducted employing ASA after oral administration in the case of the following indications:

prevention of first-instance cardiac infarction, prevention of reinfarction, treatment of unstable angina pectoris, improved patency after a bypass operation of the cardiac aorta.

Where in the following the term "anti-thrombotic therapy" is used, this substantially comprises the above indications.

In recent years, the results of these therapeutic tests on patients have been summed up (V. Fuster et al., "Aspirin in the prevention of coronary disease", New Engl. J. Med. 321, 183–185 (1989) and R. Zichner et al., "Zur optimalen Dosierung von Acetylsalicylsaeure", Med. Klin. 84, 43–51 (1989)).

ASA was first synthesized in 1853 by C. Gerhardt and is frequently employed in medical practice as a non-steroid anti-inflammatory, analgesic and antipyretic active substance. ASA influences platelet function and prevents thrombosis by irreversibly inhibiting the platelet thromboxane A2 synthesis (M. Buchanau et al.,"Aspirin inhibits platelet function independent of cyclooxygenase", Thrombosis Res. 25, 363–373 (1982)).

After oral administration ASA is quickly absorbed. However, its biological half-life in the systemic circulation is very short, it lasts only 15–20 minutes (M. Rowland et al., "Kinetics of acetylsalicyclic acid disposition in man", Nature 215, 413–414 (1967)). In normal adults ASA is quickly hydrolyzed to salicylic acid in the gastrointestinal tract. (G. Levy, "Clinical pharmacokinetics of aspirin", Pediatrics 62, 867–872 (1978)).

It should be emphasized, however, that ASA itself is active in inhibiting platelet function, and not its hydrolysis product, salicylic acid (W. Horsch, "Die Salicylate", Pharmazie 34, 585–604 (1979)).

In antithrombotic therapy oral administration is practised almost exclusively; in the case of anti-inflammatory, analgesic and antipyretic indications, however, attempts have already become known to apply the active substance via the skin. Thus, U.S. Pat. No. 3,598,122 mentions ASA as a possible antipyretic active substance in a membrane-controlled transdermal therapeutic system. FR-M 1757 describes the topical application of an oil-in-water emulsion containing 5% of ASA against acute pain. FR-A 2 297 612 claims liniments and ointments containing ASA as analgetic agent. In U.S. Pat. No. 4,012,508 ASA is employed in combination with corticosteroids for topical application in the case of dermatological indications. U.S. Pat. No. 4,219,548 describes a topical application of ASA for the checking of inflammatory processes. In European Patent 0 055 635 an ASA-containing gel is applied topically in the case of anti-inflammatory, analgesic and antipyretic indications. U.S. Pat. No. 4,460,368 discloses a device for the transdermal application of ASA out of an aqueous system to achieve anti-inflammatory and analgesic effects. In U.S. Pat. No. 4,665,063 ASA is topically applied against dermatological disturbances by using a solution in ethanol. In U.S. Pat. No. 4,640,689 an increase in the penetration rate of ASA is achieved by employing electric current. Addition of suitable penetration enhancers, as in European Patent 0 162 239, also leads to an improvement in the capacity of ASA to permeate the skin. In Japanese Publication 61 167 615 ASA is applied to the skin by means of a film. U.S. Pat. No. 4,810,699 comprises combinations of ASA with other active substances for the transdermal treatment of inflammations, pain and fever. Japanese Patent 1,203,336 relates to special penetration enhancers for the transdermal application of ASA as analgesic. Further substances of this kind for ASA in transdermal application for the checking of inflammatory processes, are contained in Japanese Patent 1,242,521. Finally, U.S. Pat. No. 4,975,269 relates to storage-stable solutions of ASA for topical application aiming at checking inflammatory processes and relieving pain.

It cannot be gathered from the mentioned prior art that the use of a transdermal system has been considered containing ASA and/or pharmaceutical salts thereof to prevent platelet aggregation in humans.

Many formulations and compositions contain water or hydrophilic solvents, which accelerate the hydrolysis of ASA to salicylic acid. Since, as explained above, salicylic acid has no antithrombotic effect but shows an anti-inflammatory and analgesic effect comparable to that of ASA, it becomes clear that the decomposition of ASA in the mentioned application systems has not been studied in detail.

It has therefore been the object of the present invention to provide an application system for the application of ASA and/or its pharmaceutically acceptable salts for antithrombotic therapy which avoids the disadvantages inherent in oral application and allows for target-specific dosage of the unchanged active substance.

This object has surprisingly been solved by employing a transdermal system for admistering acetylsalicylic acid and/or the pharmaceutically acceptable salts thereof for antithrombotic therapy.

A transdermal administration system offers the following advantages in antithrombotic therapy:

1. ASA is directly introduced into the systemic circulation in its pharmacologically active form, thus avoiding metabolism in the gastrointestinal tract.

2. reduction of gastrointestinal side effects 3. constant therapeutic effect with reduced doses of ASA 4. reduced risk of overdosage 5. treatment of outpatients without the need of observation 6. improved patient compliance.

The preferred content of ASA and/or its pharmaceutically acceptable salts in such an administration system is 5–500 mg. Suitable ASA salts are those which are non-toxic and pharmacologically effective, such as lithium, sodium, potassium, magnesium and calcium salts or salts of ASA with basic organic compounds, such as lysine, arginine or cetrimide.

In antithrombotic therapy, a therapeutically effective amount of ASA and/or ASA salts in the blood corresponds to blood level values of between 0.1 and 1.0 $\mu$g/ml. Although, after oral administration, ASA is quickly absorbed, this mode of administration is disadvantageous due to the hydrolysis of ASA to salicylic acid, especially when the short biological half-life and the necessity of constant administration are taken into account. A transdermal delivery system according to the present invention, however, ensures constant and reproducible blood levels of ASA which are effective in antithrombotic therapy. A transdermal application system of ASA and/or ASA salts according to the present invention, may be realised in various ways, for example in the form of a pressure-sensitive adhesive plaster, a film, a spray or in the form of a cream or ointment and the like. The preferred form of administration is that of a pressure-sensitive adhesive plaster comprising an impermeable backing layer, an active substance reservoir connected thereto and consisting of a polymer matrix, where other control mechanisms are not present a membrane controlling the release of active substance, a pressure-sensitive adhesive device for fixing the system to the skin and, if required, a protective layer which may be detached prior to the application of the system. In all these cases, the matrix forming the reservoir must be chosen such that hydrolysis of ASA is precluded or is at least greatly reduced. A hydrophobic adjustment of the matrix is more suitable for this purpose than a hydrophilic one. The transdermal pressure-sensitive adhesive plasters suitable for this invention are all known to the man skilled in the art from the prior art. For the most part, these plasters can be assigned to two basic control principles: matrix diffusion control and membrane control, whereby only the latter allows for an active substance release of zero order. A matrix diffusion control plaster is described, for example, in German Patent No. 33 15 272. It comprises an impermeable backing layer, an especially constructed reservoir connected thereto consisting of a polymer matrix, said reservoir containing the active substance in a concentration which is above the saturation concentration, a pressure-sensitive adhesive layer connected to the reservoir and permeable to the active substance and a protective layer which covers the pressure-sensitive adhesive layer and may be detached for application of the system. If the reservoir matrix itself is pressure-sensitive adhesive, the additional pressure-sensitive adhesive layer need not be present. Examples for plasters with membrane control include U.S. Pat. Nos. 3,742,951, 3,797,494, 3,996,934 and 4,031,894. These plasters in principle consist of a backing layer which forms one of the surfaces, an adhesive layer permeable to the active substance which forms the other surface and, finally, a reservoir containing the active substance between the two layers forming the surfaces. Alternatively, the active substance may be contained in a plurality of microcapsules dispersed within the permeable adhesive layer. In all cases, the active substance is continuously released through a membrane from the reservoir or the microcapsules into the adhesive layer which, is permeable to the active substance and which is in contact with skin of the person or warm blooded animal to be treated. In case of microcapsules, the capsule material may also serve as a membrane.

In addition, it should be pointed out that control is also possible by means of electric current, whereby the velocity is dependent on the phase in which the active substance permeates the skin. Such processes are referred to as electroosmosis, iontophoresis or electrophoresis.

All types of plasters may, if required, contain various additives in addition to the matrix and the active substance in order to achieve the desired properties. To be mentioned in particular are those additives enhancing the permeation of ASA and/or its pharmaceutically acceptable salts through the skin. The various suitable additives are obvious to the man skilled in the art and are therefore not listed herein.

The present invention will be illustrated but not limited by the following examples:

EXAMPLES

1. Acrylate-based Single-Layer System 5 g of dioctyl cyclohexane, 8 g of acetylsalicylic acid and 40 mg acetic anhydride are added to 100 g of a solution of an acrylic adhesive (e.g. Durotak R 280-2516 National Starch and Chemical) having a solids content of 41 parts by weight; the solution is homogenized by agitating.

The solution is thereafter spread at a thickness of 300 $\mu$m on a 100 $\mu$m thick siliconized polyester film. In the finished system, this film takes over the function of the detachable protective layer and must be removed prior to use. The moist film is dried for 20 minutes at 50° C. and thereafter has a gsm substance of 100 g/m².

The dried film is subsequently laminated with a 12 $\mu$m thick polyester film and the finished plasters are punched out of the laminate.

2. Multilayer System

The finished system comprises a detachable protective layer, a spread of skin adhesive, a non-adhesive reservoir, a backing layer impermeable to active substance and a basic spread, having good viscous properties, which is present between the reservoir layer and the backing layer and performs the function of fixing the non-adhesive reservoir to the backing layer.

A. Manufacture of the Skin Adhesive Spread 100 parts of a block polymer consisting of polystyrene and polyisoprene (e.g. Cariflex TR-1107, Fa. Shell)

175 parts of a glycerol ester of partially hydrogenated colophonium and 50 parts of dioctyl cyclohexane are dissolved in 500 g n-heptane and subsequently added to 15 g acetylsalicylic acid and 150 mg acetic anhydride. The mass is homogenized by agitating and then spread on a siliconized polyester film at a thickness of 100 $\mu$m, the polyester film serving in the finished product as a detachable protective layer. The moist film is dried for 20 minutes at 50° C. and thereafter has a gsm substance of 25 g/m².

B. Manufacture of the Reservoir Spread 100 parts of a block polymer consisting of polystyrene and polyisoprene (e.g. Cariflex TR-1107, Fa. Shell)

and 20 parts dioctyl cyclohexane are dissolved in 120 g n-heptane.

Thereafter, 40 parts of acetylsalicylic acid and 40 mg acetic anhydride are added and the mass is homogenized by agitating. The resulting mass is spread at a thickness of 300 $\mu$m on a protective polyester film which is siliconized to a higher degree than the detachable protective layer, and is dried for 20 minutes at 50° C. The dried reservoir layer has a gsm substance of 100 g/m²

C. Manufacture of the Basic Spread 100 parts of a block polymer consisting of polystyrene and polyisoprene (e.g. Cariflex TR-1107, Fa. Shell)

175 parts of a glycerol ester of partially hydrogenated colophonium and 50 parts of dioctyl cyclohexane are dissolved in 500 g n-heptane and, analogous to B, spread at a thickness of 100 $\mu$m onto a polyester film which is siliconized to a higher degree than the detachable protective layer and is dried for 20 minutes at 50° C. The dried film has a gsm substance of 25 g/m²

D. Assembly of the Entire System and Punching of the Individual Plasters

The reservoir spread resulting from B is laminated onto the skin adhesive spread. The foil which is siliconized to a higher degree is thereafter removed. Then the basic spread is applied in the same manner and after removal of the film which has a higher degree of siliconization, a 12 μm thick polyester film is laminated thereon.

The finished plasters are punched out of the finished laminate.

3. Membrane System

A heat-sealing laminate consisting of a flexible polyester film and a film of a polyethylene/vinylacetate copolymer is sealed against a 50 cm thick membrane of a polyethylene/vinylacetate copolymer, having a vinyl acetate content of 19%, in the dimensions and shapes corresponding to those of the intended plasters and in such a manner that a kind of flat bag is obtained. The sealing seam is to be 4 mm in width. Before the bag is sealed in such a manner that no gaps remain, it is filled with a preparation of silicone oil with 10% of acetylsalicylic acid and 0.05% of acetic anhydride. The membrane side of the bag is then laminated on a silicone-based skin adhesive spread, which is present on a suitable foil having been rendered adhesive. This foil is identical with the detachable protective layer.

The finished systems are punched out in such a manner that a bag having a sealing border of 3 mm in width remains.

I claim:

1. A transdermal therapeutic application system useful for antithrombotic therapy, for applying through the skin of a warm-blooded animal, an effective antithrombotic amount of an active ingredient consisting essentially of acetyl salicylic acid or a non-toxic pharmaceutically acceptable salt thereof or a combination thereof;

said transdermal therapeutic application system consisting essentially of a hydrophobic polymer matrix such that hydrolysis of acetyl salicylic acid is precluded;

said system containing a solvent selected from the group consisting of dioctyl cyclohexane, dioctyl cyclohexane dissolved in n-heptane, glycerol ester of partially hydrogenated colophonium and dioctyl cyclohexane dissolved in n-heptane, and silicone oil.

2. A transdermal therapeutic application system useful for antithrombotic therapy, for applying through the skin of a person, an effective antithrombotic amount of an active ingredient combination consisting essentially of acetyl salicylic acid or a non-toxic pharmaceutically acceptable salt thereof or a combination thereof; and acetic anhydride;

said transdermal therapeutic application system consisting essentially of a hydrophobic polymer matrix such that hydrolysis of acetyl salicylic acid is precluded;

said system containing a solvent selected from the group consisting of dioctyl cyclohexane, dioctyl cyclohexane dissolved in n-heptane, glycerol ester of partially hydrogenated colophonium and dioctyl cyclohexane dissolved in n-heptane, and silicone oil.

3. The transdermal therapeutic application system of claim 2, wherein said effective antithrombotic amount comprises from 5 to 500 mg of acetyl salicylic acid, or a non-toxic pharmaceutically acceptable salt thereof or a combination thereof.

4. The transdermal therapeutic application system of claim 2, comprising an impermeable backing layer;

said matrix being an active substance reservoir connected thereto and made of polymer;

a membrane controlling the release of the active ingredient;

a pressure-sensitive adhesive device for fixing the system to the skin; and a protective layer which may be detached prior to the application of the system.

5. The transdermal therapeutic application system of claim 2, wherein said active ingredient is contained in a cream or an ointment.

6. The transdermal therapeutic application system of claim 2, further comprising means for providing an electric current for enhancing the permeation of acetyl salicylic acid or a non-toxic pharmaceutically acceptable salt through the skin.

7. A therapeutic method for preventing thrombosis in a warm-blooded animal, comprising administering through a transdermal therapeutic application system applied to the skin of said animal, an effective antithrombotic amount of an active ingredient consisting essentially of acetyl salicylic acid or a non-toxic pharmaceutically acceptable salt thereof or a combination thereof;

said transdermal application system comprising a hydrophobic polymer matrix such that hydrolysis of acetyl salicylic acid is precluded;

said system containing a solvent selected from the group consisting of dioctyl cyclohexane, dioctyl cyclohexane dissolved in n-heptane, glycerol ester of partially hydrogenated colophonium and dioctyl cyclohexane dissolved in n-heptane, and silicone oil.

8. A therapeutic method for preventing thrombosis in a warm-blooded animal, comprising administering through a transdermal therapeutic application system applied to the skin of said animal, an effective antithrombotic amount of an active ingredient combination consisting essentially of acetyl salicylic acid or a non-toxic pharmaceutically acceptable salt thereof or a combination thereof; and acetic anhydride;

said transdermal therapeutic application system comprising a hydrophobic polymer matrix such that hydrolysis of acetyl salicylic acid is precluded;

said system containing a solvent selected from the group consisting of dioctyl cyclohexane, dioctyl cyclohexane dissolved in n-heptane, glycerol ester of partially hydrogenated colophonium and dioctyl cyclohexane dissolved in n-heptane, and silicone oil.

9. The therapeutic method of claim 8, wherein said non-toxic pharmaceutically acceptable salt is selected from the group consisting of lithium, sodium, potassium, magnesium, calcium, lysine, arginine, and cetrimide.

10. The therapeutic method of claim 8, wherein said effective amount of acetyl salicylic acid, or said salt thereof, in the blood of said warm-blooded animal is between 0.1 and 1.0 μm/ml.

11. Transdermal therapeutic application system for antithrombotic therapy, characterized in that it contains as the only active ingredient acetylsalicylic acid in the form of a pharmaceutically acceptable salt thereof, a hydrophobic polymer matrix and additionally acetic anhydride.

12. The transdermal therapeutic application system of claim 11 which contains as active ingredient acetylsalicylic acid in the form of a pharmaceutically acceptable salt thereof together with free acetylsalicylic acid.

13. A therapeutic method for preventing thrombosis in a person comprising administering through a transdermal therapeutic application system applied to the skin of the person, an effective antithrombotic amount of an active ingredient consisting essentially of acetyl salicylic acid or a non-toxic pharmaceutically acceptable salt thereof or a combination thereof;

said transdermal application system consisting essentially of a hydrophoblic polymer matrix such that hydrolysis of acetyl salicylic acid is precluded;

said system containing a solvent selected from the group consisting of dioctyl cyclohexane, dioctyl cyclohexane dissolved in n-heptane, glycerol ester of partially hydrogenated colophonium and dioctyl cyclohexane dissolved in n-heptane, and silicone oil.

14. A therapeutic method for preventing thrombosis in a person comprising administering through a transdermal therapeutic application system applied to the skin of the person, an effective antithrombotic amount of an active ingredient combination consisting essentially of acetyl salicylic acid or a non-toxic pharmaceutically acceptable salt thereof or a combination thereof; and acetic anhydride;

said transdermal application system consisting essentially of a hydrophobic polymer matrix such that hydrolysis of acetyl salicylic acid is precluded;

said system containing a solvent selected from the group consisting of dioctyl cyclohexane, dioctyl cyclohexane dissolved in n-heptane, glycerol ester of partially hydrogenated colophonium and dioctyl cyclohexane dissolved in n-heptane, and silicone oil.

15. The transdermal therapeutic system of claim 11, characterized in that it additionally contains a solvent.

* * * * *